US009222855B2

(12) United States Patent
Chaintreau et al.

(10) Patent No.: US 9,222,855 B2
(45) Date of Patent: Dec. 29, 2015

(54) VOLATILE COMPOUNDS TRAP DESORPTION DEVICE AND METHOD FOR DESORBING VOLATILE COMPOUNDS FROM A TRAP

(75) Inventors: Alain Chaintreau, Geneva (CH); Frédéric Begnaud, Geneva (CH); Urs Keller, Genolier (CH)

(73) Assignee: Firmenich SA, Geneva (CH)

( * ) Notice: Subject to any disclaimer, the term of this patent is extended or adjusted under 35 U.S.C. 154(b) by 310 days.

(21) Appl. No.: 13/820,741

(22) PCT Filed: Sep. 1, 2011

(86) PCT No.: PCT/EP2011/065115
§ 371 (c)(1),
(2), (4) Date: Mar. 4, 2013

(87) PCT Pub. No.: WO2012/031975
PCT Pub. Date: Mar. 15, 2012

(65) Prior Publication Data
US 2013/0167616 A1    Jul. 4, 2013

(30) Foreign Application Priority Data
Sep. 6, 2010    (EP) .................................... 10175432

(51) Int. Cl.
*G01N 1/22*    (2006.01)
*G01N 1/40*    (2006.01)
(Continued)

(52) U.S. Cl.
CPC .............. *G01N 1/22* (2013.01); *B01J 20/3425* (2013.01); *B01J 20/3458* (2013.01); *B01J 20/3483* (2013.01); *G01N 1/2214* (2013.01); *G01N 1/405* (2013.01); *G01N 33/0004* (2013.01); *B01D 53/04* (2013.01); *B01D 2257/90* (2013.01);
(Continued)

(58) Field of Classification Search
CPC ....... G01N 1/22; G01N 1/2214; G01N 1/405; G01N 33/0004
USPC ............................................. 73/23.34, 23.41
See application file for complete search history.

(56) References Cited

U.S. PATENT DOCUMENTS 4,374,476 A * 2/1983 Ford ............................. 73/23.42
5,088,335 A    2/1992 Lafreniere et al.
(Continued)

FOREIGN PATENT DOCUMENTS

WO    WO 99/66305 A1    12/1999

OTHER PUBLICATIONS

International Search Report and Written Opinion of the International Searching Authority, application No. PCT/EP2011/065115, mailed on Nov. 16, 2011.
(Continued)

*Primary Examiner* — Peter Macchiarolo
*Assistant Examiner* — Alexander Mercado
(74) *Attorney, Agent, or Firm* — Winston & Strawn LLP

(57) ABSTRACT

A method for restoring a volatile compound from a trapping means, wherein the method includes a flowing step wherein a carrier gas flows through the trapping means, at a controlled rate, by increasing the volume of a chamber located downstream of the trapping means is disclosed. The invention also relates to a device for implementing the method. The invention allows to faithfully restore the compounds that have been previously trapped and to faithfully restore the trapped odors.

20 Claims, 5 Drawing Sheets

(51) Int. Cl.
 *G01N 33/00* (2006.01)
 *B01J 20/34* (2006.01)
 *B01D 53/04* (2006.01)

(52) U.S. Cl.
 CPC ............... *B01D 2258/0275* (2013.01); *B01D 2259/40086* (2013.01)

(56) References Cited

U.S. PATENT DOCUMENTS

| | | | |
|---|---|---|---|
| 5,110,214 A * | 5/1992 | Battiste et al. | 374/45 |
| 5,150,601 A * | 9/1992 | Simeroth et al. | 73/23.41 |
| 5,237,852 A * | 8/1993 | Kolpak | 73/23.2 |
| 6,649,129 B1 | 11/2003 | Neal | |
| 7,552,617 B2 * | 6/2009 | Danilchik | 73/23.41 |
| 2003/0172718 A1 * | 9/2003 | Lee et al. | 73/23.41 |
| 2008/0016944 A1 * | 1/2008 | Legrand | 73/25.01 |
| 2008/0028827 A1 * | 2/2008 | Andrews et al. | 73/23.2 |
| 2009/0158820 A1 * | 6/2009 | Bostrom et al. | 73/61.53 |
| 2010/0107730 A1 * | 5/2010 | Aono | 73/23.39 |
| 2014/0033835 A1 * | 2/2014 | Hendrikse et al. | 73/863.12 |

OTHER PUBLICATIONS

Regal et al., "Solid Phase Microextraction (SPME) of Orange Juice Flavor: Odor Representativeness by Direct Gas Chromatography . . . " J.Agric. Food Chem. (2003) 51:7092-7099.

Chaintrain et al. "Determination of Partition Coefficients and Quantitation of Headspace Volatile Compounds" Anal. Chem. 1995, 67:3300-3304.

* cited by examiner

VOLATILE COMPOUNDS TRAP DESORPTION DEVICE AND METHOD FOR DESORBING VOLATILE COMPOUNDS FROM A TRAP

This application is a 371 filing of International patent application no. PCT/EP2011/065115 filed Sep. 1, 2011, which claims priority to European patent application no. 10175432.3 filed Sep. 6, 2010.

BACKGROUND

The invention relates to the field of catching, analyzing and reproducing odors, for example odors from natural materials such as plants or fruits. The invention relates more accurately to a volatile compound trap desorption device and to a method for desorbing volatile compounds from a trap, the volatile compounds being previously trapped in the trap. The invention also relates to the release of the volatile compounds from the trap, in a manner making it possible to faithfully reproduce the trapped odor of the material releasing the volatile compounds.

SUMMARY OF THE INVENTION

Catching, analyzing and reproducing natural odors or more accurately the mixture of volatile compounds that characterize the overall odor of natural materials is still one of the preferred ways to add new olfactive notes and accords to the perfumers' palette. Volatiles emitted by living plants or fruits are best sampled in-situ since cutting the plant for example changes enzymatic processes responsible for the formation of the overall odor of the plant, by altering the nature and composition of odorant compounds forming the perceived odor. That is why treks involving olfactive experts are still organized to capture odors from all over the world. Using different portable trapping systems (adsorbent traps, SPME, etc.), it is possible to collect the so-called "headspace" i.e. the mixture of volatiles emitted by the plant or fruit and constituting their perceived odors, to analyze it, but the reconstitution of the latter in a faithful manner, for delivery in the laboratory and the availability to the perfumer or evaluator, is still not possible with current techniques. Prior known techniques for sampling and desorbing odors trapped from plants and fruits, even when used in-situ, do not allow faithful reproduction of the global odor of the targeted plant or product. No device exists allowing a later faithful delivery of the captured odor in a laboratory for thorough olfactive evaluation. Moreover, there is currently no way to verify the representativeness of an odorant sample before further analytical study. Thus, a goal is to be able to olfactively evaluate faithful and accurate odorant mixtures of volatiles captured in nature in an up-to-date equipped laboratory. This implies an exhaustive desorption of the volatile compounds.

It is preferred not to use a desorption solvent, since the latter brings artifacts into the mixture released as compared to the trapped one. Even if representative trapping techniques are used, there is currently no method available for desorbing volatile compounds and providing them in a suitable way for further organoleptic and/or analytical evaluation, and there is no method for faithfully restoring or reconstituting the trapped mixture of volatiles responsible for the natural odor of the targeted plant or fruit.

From "Solid Phase Microextraction (SPME) of Orange Juice Flavor: Odor Representativeness by Direct Gas Chromatography Olfactometry (D-GC-O)" published in "Journal of agricultural and food chemistry" 2003, 51, 7092-7099, a desorption device is already known. It includes a heating means for heating a trap containing volatile compounds and guiding means for guiding a carrier gas flow through the trap to a means for evaluating the desorbed compounds. However, these compounds are only available at the evaluating means for a few seconds. This is a problem especially when the evaluating means is a sniffing port. Moreover, with such a technique, the odors released from the trap cannot be satisfactorily evaluated because their intensity permanently varies throughout the evaluation period, thus modifying perception. Furthermore, the concentration of the delivered volatile compounds cannot be controlled. Faithful reproduction of the overall odor mixtures, as collected on the trap, is therefore impossible.

The aim of the invention is to provide a desorbing method and a desorbing device that overcomes these drawbacks and that improves the desorbing methods and the desorbing devices that are known from the prior art. In particular, the desorbing method and the desorbing device according to the invention make it possible to accurately restore in the laboratory odors that have been captured in nature and to evaluate and reproduce them in the form of a mixture of volatiles which really corresponds to the trapped odor of the targeted product.

The desorbing method according to the invention is defined by claim 1.

Various embodiments of the desorbing method are defined by the dependent claims 2 to 9.

The desorbing device according to the invention is defined by claim 10.

Various embodiments of the desorbing device are defined by the dependent claims 11 to 18.

Moreover, the invention relates to a data medium comprising a software for implementing the previously defined method.

The invention also relates to a computer program comprising a computer program code means suitable for implementing the steps of the desorbing method defined previously, when the program runs on a computer.

The appended drawing shows, by way of example, two embodiments of a desorption device according to the invention, one embodiment of a sensory evaluation device according to the invention, one embodiment of a desorbing method according to the invention and one embodiment of a sensory evaluation method according to the invention.

FIG. 1 is a schematic view of a first embodiment of a desorption device according to the invention in a first configuration.

FIG. 2 is a schematic view of the first embodiment of the desorption device according to the invention in a second configuration.

FIGS. 3 to 7 are schematic views illustrating an embodiment of the desorbing method according to the invention.

FIG. 8 is a flowchart of an embodiment of the desorbing method according to the invention.

FIG. 9 is a flowchart of an embodiment of the sensory evaluation method according to the invention.

FIG. 10 is a schematic view of another embodiment of a desorption device according to the invention in a first configuration.

A first embodiment of a desorption device 1 according to the invention is described hereinafter with reference to FIGS. 1 and 2. The desorption device allows to restore or desorb a volatile compound or volatile compounds that are trapped in a trapping means or a trap 8, for example a trap containing Tenax® sorbent, i.e. to release volatile compounds from the trap. The volatile compound(s) may be pleasant or unpleasant. The device allows to restore the trapped volatile compounds trapped in the trap, i.e.—by "restore" or "restoring" it is meant here to desorb exhaustively the volatile compounds trapped in the trap or at least to desorb the different volatile compounds, present in the trapped mixture, in the same relative proportion, so that the composition of the mixture of volatile compounds in the trap before desorption and the composition of the mixture in the chamber after desorption is the same. Thus, the odor of the trapped composition is not altered by the desorption step.

The device includes a closed chamber 30 having a volume that can be modified, securing means 6, 7 for securing the trap 8 to the device, a flow splitter 9 supplied with a carrier gas, such as an inert gas regarding volatile compounds that are trapped in the trap, for example dinitrogen $N_2$ and a circuit for guiding gases from the flow splitter to the closed chamber through the trap when the volume of the chamber is increased. The chamber is closed but has an aperture that allows the gas to reach the chamber from the trap. The flow splitter divides the flow of the carrier gas into two streams: a stream towards the chamber and a stream towards the atmosphere. The device also includes a controlling means 20, 21, 22 for controlling the volume of the chamber. For example, the controlling means comprises an actuator 20, 21 controlled by a logic processing unit 22, for example a logic processing unit included in a computer. The actuator may include a motor 20 and a transmission means 21 linking the motor to a wall of the chamber so that the wall is deformed and/or moved when the motor is activated.

BRIEF DESCRIPTION OF THE DRAWINGS

In the device of FIGS. 1 and 2, the chamber includes a cylinder 2 and a piston 3, the piston being movable in the cylinder according to the axis of the cylinder. In this embodiment, the piston is a movable wall of the chamber, the volume of the chamber being increased when the piston is moved upward and the volume of the chamber being decreased when the piston is moved downward. The transmission means may include a screw and nut system for transforming the rotation movement of the motor to a translation movement of the piston. The extreme positions of the piston in the cylinder may be defined by sensors 23 and 24. An arm 25 secured to the piston, especially secured to a rod 4 of the piston, may activate a switch of the upper sensor 23 when the piston is in its upper position, i.e. when the volume of the chamber is maximum and may activate a switch of the lower sensor 24 when the piston is in its lower position, i.e. when the volume of the chamber is minimum.

At the top of the rod 4, a securing means 6 allows to secure the trap to the rod. Another securing means 7 allows to secure and connect the trap to the flow splitter 9. Thus, when the trap is secured to the desorption device, particularly to the flow splitter 9 of the desorption device and to the rod of the piston of the desorption device, the carrier gas supplied to the flow splitter 9 can arrive in the chamber through the trap and a through-hole 5 in the piston rod 4. The flow rate of the carrier gas supplied to the flow splitter is such that only a part of the carrier gas supplied go to the chamber through the above-mentioned circuit, the other part of the carrier gas flows out from the desorption device at the level of the flow splitter. The device also includes a means for controlling the flow rate of the carrier gas supplied to the flow splitter. For example, the logic processing unit may include such a means for controlling the flow rate of the carrier gas that may be directly linked to the motion speed of the piston.

Figure 1:
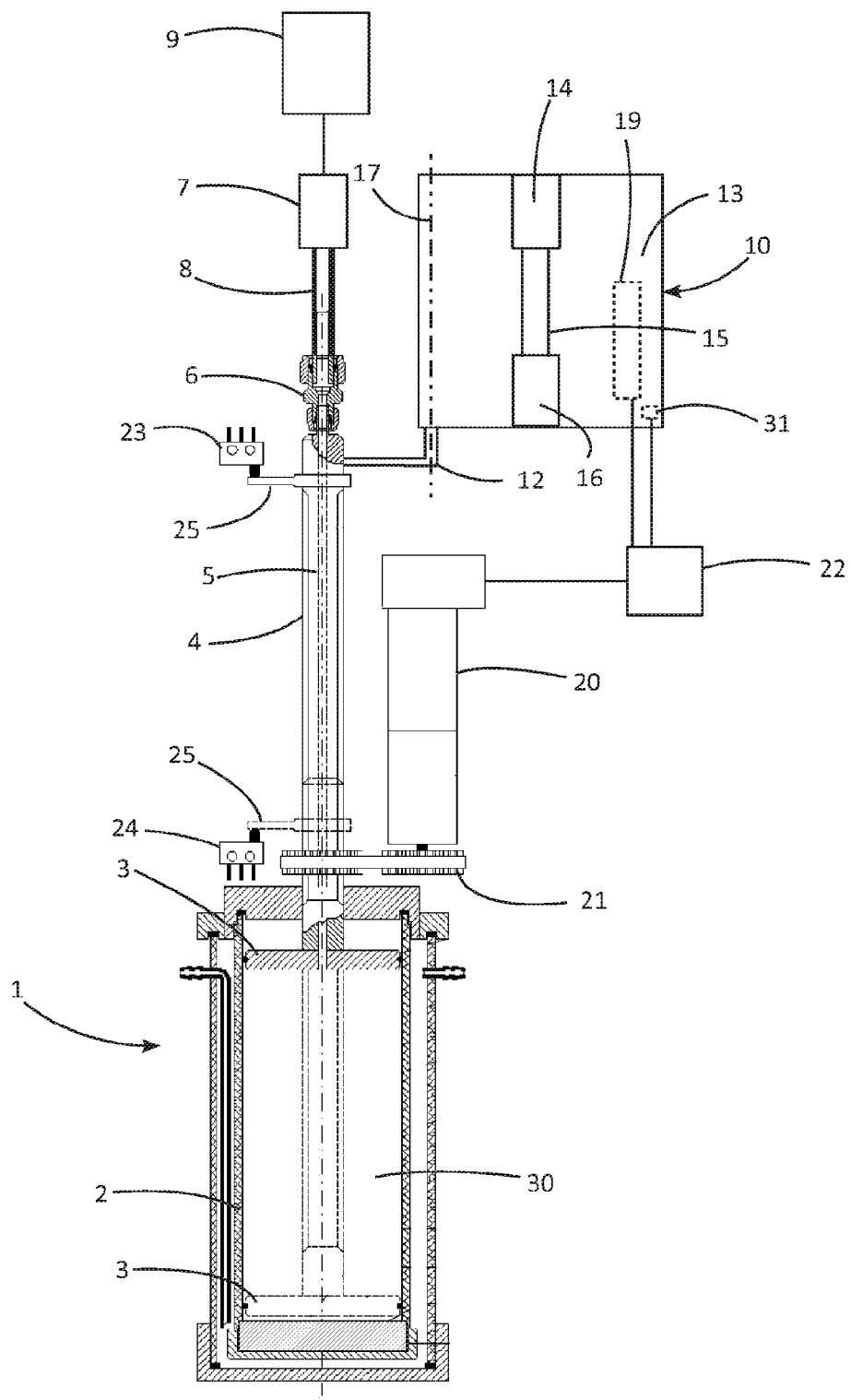

The desorption device also includes a heating means 10 having a first configuration for not heating the trap and a second configuration for heating the trap. For instance, the heating means 10 is movable between a first position remote from the trap (see FIG. 1) and corresponding to the first configuration and a second position close to the trap (see FIG. 2) and corresponding to the second configuration. The heating means may be rotatably mounted on a holder 12 secured to the rod. Moreover, the heater of the heating means may be deactivated in the first configuration and may be activated in the second configuration. Alternately, the holder may be secured on the means 6 for securing the trap or on any element directly or indirectly secured to this securing means. Thus, the heating means may rotate about an axis 17 defined by the holder 12. For example, the axis 17 is parallel or substantively parallel to the axis of the trap when mounted on the desorption device. When the heating means is in its first configuration, it does not heat the trap. The trap is cold, for example the temperature of the trap is the ambient temperature. When the heating means is in its second configuration, it does heat the trap. The trap is hot, for example the temperature of the trap rise from the ambient temperature to a high temperature, for example a temperature comprised between 100° C. and 300° C., especially a temperature of about 250° C.

The heating means includes an inertial element 13, for example a metallic inertial element, especially made of an alloy such as an aluminum alloy. The inertial element includes an articulation means via which it is mechanically connected to the holder.

DETAILED DESCRIPTION OF THE PREFERRED EMBODIMENTS

The inertial element includes a heater 19 such as an electric resistor whose power supply is controlled by a logic processing unit, for example the above-mentioned logic processing unit 22. The inertial element also includes a temperature sensor 31 connected to the logic processing unit controlling the heater. Preferably, the heater is electrically supplied as a function of the temperature of the inertial element. The heater may be deactivated in the first configuration and activated in the second configuration.

A side of the inertial element has a cut out 14, 15, 16. The middle part 14 of the cut out surrounds at least a portion of the trap 8 when the heating means is in its second position. Optionally, the upper part 14 of the cut out surrounds at least a portion of the upper securing means 7 when the heating means is in its second position. Optionally, the lower part 15 of the cut out surrounds at least a portion of the lower securing means 6 when the heating means is in its second position. The cut out has preferably a U shape so as to surround the trap and the securing means.

The inertial element may be coated with a thermal insulating material except at the level of the cut out. It is the heat radiation and conduction from the surface of the cut out that heats the trap when the heating means is in its second configuration (see FIG. 2).

A known device designed for loading traps with volatile compounds and comprising a chamber closed by a piston and a cylinder may be modified so that it can be used as a desorption device according to the invention. For example, a static- and trapped headspace cell (S&T-HSCell) Static and trapped headspace cell as described in Chaintreau et al., Anal Chem 1995, 3300 may be used.

The cylinder and the piston may be constituted of inert components such as stainless steel or glass. The components may be treated or not for inertness towards potential surface adsorption. Particularly, the components may be coated or not for inertness towards potential surface adsorption. According to certain embodiments of the invention, one or more of the surfaces of the stainless steel components are passivated. For example, the surface may be coated or subjected to a treatment of the Sulfinert® type (Sulfinert® is a trade mark of the company Restek Performance Coatings, Bellefonte, Pa. 16823, USA).

In the first embodiment, the heating means is mobile in translation regarding the cylinder.

The desorption device includes hardware and software means for implementing the method according to the invention, i.e. includes hardware and/or software means for making the desorption device to operate such that the method is implemented. Especially, the desorption device includes a control means for controlling the variation of the volume of the chamber and thus controlling the flow rate of the carrier gas through the trapping means. The desorption device also includes a control means for controlling the heating of the trap. The software means may include computer software.

A second embodiment of a desorption device (not represented) according to the invention differs from the above described device in that a through-hole is provided in a stationary wall i.e. in a wall that is not moved for increasing or decreasing the volume of the chamber. In this embodiment, there is no through-hole in the piston. A securing means on this stationary wall allows to secure the trap to the chamber. Another securing means allows to secure and connect the trap to a flow splitter. Thus, when the trap is secured to the desorption device, particularly to the flow splitter of the desorption device and to the stationary wall of the desorption device, the carrier gas supplied to the flow splitter can arrive in the chamber through the trap and a through-hole in the stationary wall. In such an embodiment, the heating means may not be mobile in translation regarding the chamber. The design of such an embodiment may allow to avoid cold spots on the carrier gas path dowstream the trap.

Figure 10:
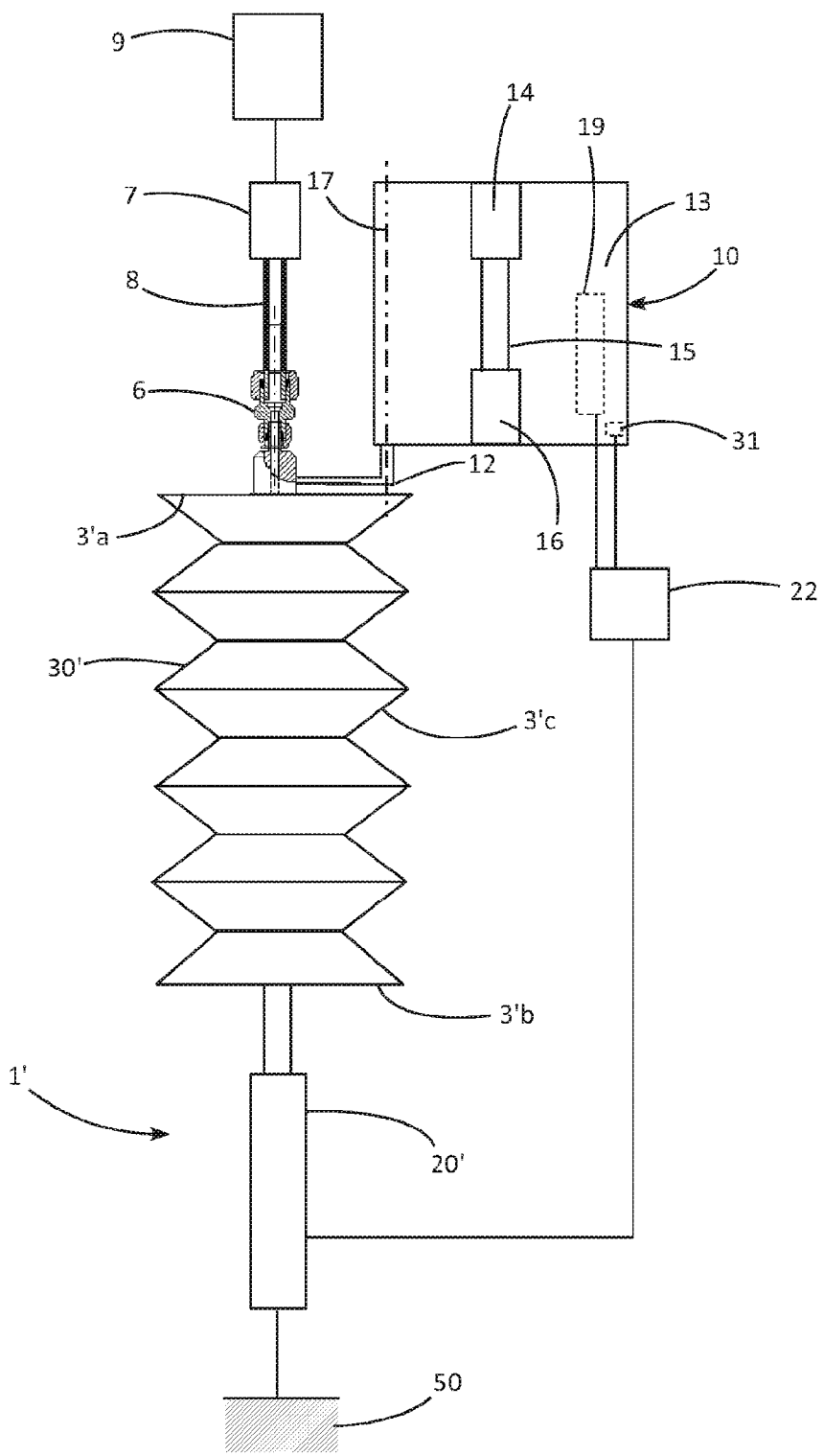

A third embodiment of a desorption device 1' according to the invention is represented on FIG. 10. It differs from the first and second embodiments in that the chamber 30' comprises a deformable wall 3'c.

The chamber also includes a stationary wall 3'a and a mobile wall 3'b. The deformable wall is deformed by action of an actuator 20' controlled by a logic processing unit 22. The mobile wall is moved by action of the actuator 20'. The actuator allows to move the mobile wall as regards to a frame 50 and thus to move the mobile wall as regards to the stationary wall. Thus, the deformable wall is deformed by activation of the actuator. For example, the deformable wall may be a bellows.

In the three above-described embodiments, the heating means may comprise an infrared heater. The infrared heater of the heating means may be deactivated in the first configuration and may be activated in the second configuration. The heating means may be in the same position in the first and second configurations.

A support may be provided for holding the heating means remote from the trap when no heating is needed, particularly during a step of removing the trap from the device.

Figure 7:
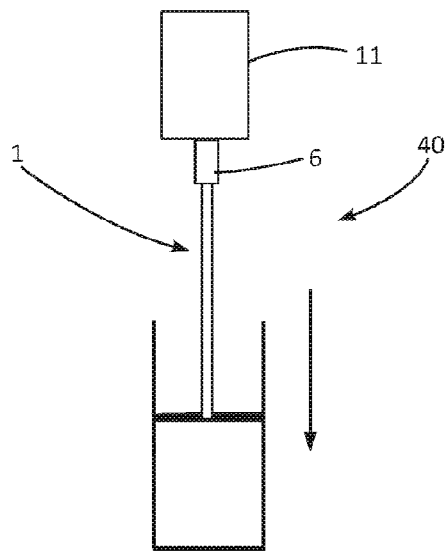
Figure 8:
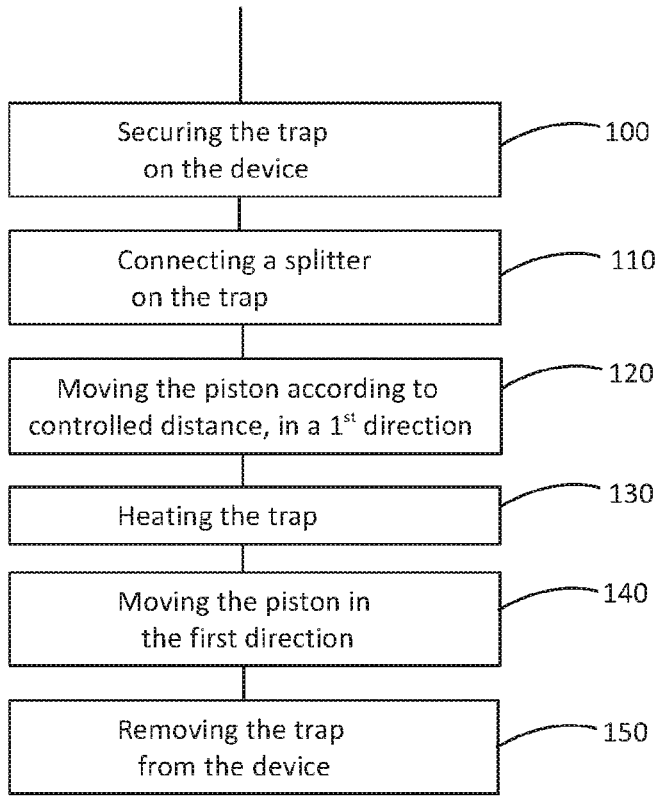

An embodiment of a device 40 for sensory evaluating a volatile compound trapped in a trap is represented on FIG. 7. The evaluation device comprises a desorption device according to the invention and a sensory evaluation means 11, for example a sniffing port, the analyzing means being connected to the desorption device.

An embodiment of the desorbing method according to the invention is described hereinafter. The method allows to restore or desorb a volatile compound or volatile compounds that are trapped in a trapping means or a trap 8. The method comprises a flowing step wherein the carrier gas flows through the trap, at a controlled rate, by increasing the volume of the chamber located downstream of the trap. It is the increase of the volume of the chamber that causes the carrier gas flow through the trap.

The flow rate of the carrier gas is controlled through the control of the variation of the volume of the chamber. The modification of the volume of the chamber may be caused by a controlled deformation of a wall of the chamber and/or a controlled movement of a wall of the chamber. Especially, with the above-described embodiment of the desorption device, the volume of the chamber is modified by a controlled movement of the piston in the cylinder: an upward controlled movement of the piston to increase the volume of the chamber and a downward controlled movement to decrease the volume of the chamber.

The flow rate of the carrier gas in the trap drives the volatile compounds that are desorbed from the trap and conduct them in the chamber 30. To this end, the trap is preferably heated by the heating means when the carrier gas flows through the trap. Preferably, the transfer of volatile compounds from the trap to the chamber implies two steps: desorbing the compounds and conveying them from the trap to the chamber. The chamber may be maintained at a given temperature.

Desorbing compounds from the trap involves shifting the partition coefficient of the compounds to lower their affinity for the sorbent. For example, heating the trap drastically modifies the partition coefficient values. This is the most convenient technique to directly desorb compound into a gas phase. To be efficient, the following rules should be observed:
- homogeneous heating of the entire trap during the desorption process,
- no overheating to avoid degradation of compounds,
- stable temperature at equilibrium, and
- reproducible temperature profile.

Additional requirements should also be taken into account:
- The trap should be directly connected to the piston to limit the length of the path that the desorbed compounds have to follow to reach the chamber.
- The heating means should follow the piston movement. This implies a light heating means secured to the piston or to an element moving with the piston.
- Due to the geometry of the controlling means, the heating means may be close to the controlling means. Hot parts should not affect the operating of the controlling means.
- The desorption temperature should be reached in less than 2 minutes. Quickness is essential to get an exhaustive desorption of the trap during the short lapse of time available to raise entirely the piston.
- Cold spots should not exist on the path that desorbed compounds follow to reach the chamber. To this end, the piston and/or the cylinder may be heated to avoid cold spot and/or adsorptions.

The flowing step preferably includes a first flowing sub-step during which the trap is not heated. During this first sub-step, the inert carrier gas flows through the trap and conveys oxygen and water that may be contained in the trap. If not purged from the trap, oxygen may cause an oxidation of the volatile compounds contained in the trap when it is heated. As for the water, at least a certain amount of purging can also be beneficial. Water may cause hydrolysis of certain volatile compounds contained in the trap when it is heated. However, some moisture in the carrier gas may also be helpful to avoid adsorption of other volatile compounds when they are released in the chamber. The level of moisture needed in the carrier gas may therefore be dependent on the nature of the volatile compounds and the skilled person can adjust the moisture level as a function of the nature of the material being captured so as to produce a restored mixture of volatiles that is as faithful to the captured material as possible.

The flowing step preferably includes a second flowing sub-step during which the trap is heated. During this second sub-step, the inert carrier gas flows through the trap and convey the thermally desorbed compounds so that they reach the chamber.

The second flowing sub-step may comprise switching the heating means from the first configuration to the second configuration. For example, the heating means is moved, by action of an operator, from the first position remote from the trap to a second position close to the trap, especially a second position in which the heating means surrounds the trap at least partially.

An embodiment of a sensory evaluation method according to the invention is described hereinafter. The method may include:
- a desorption step including the implementation of the desorbing method of the invention,
- a step of removing the trap from the desorption device,
- a step of connecting the chamber to a sensory evaluation means 11,
- a step of transferring the compounds contained in the chamber from the chamber to the sensory evaluation means, at a controlled rate, by decreasing the volume of the chamber.

It is the decrease of the volume of the chamber that causes the content of the chamber to be transferred from the chamber to the sensory evaluation means. The compounds contained in the chamber include the carrier gas and the desorbed volatile compounds that have been released from the trap. The flow rate of these compounds is controlled through the control of the volume of the chamber. As during the desorption step, the modification of the volume of the chamber may be caused by a controlled deformation of a wall of the chamber and/or a controlled movement of a wall of the chamber. Especially, with the above-described embodiment of the desorption device, the volume of the chamber is modified by a controlled movement of the piston in the cylinder: an upward controlled movement of the piston to increase the volume of the chamber and a downward controlled movement to decrease the volume of the chamber.

When the compounds reach the sensory evaluation means, they are evaluated. The analysis may include an organoleptic evaluation.

Figure 2:
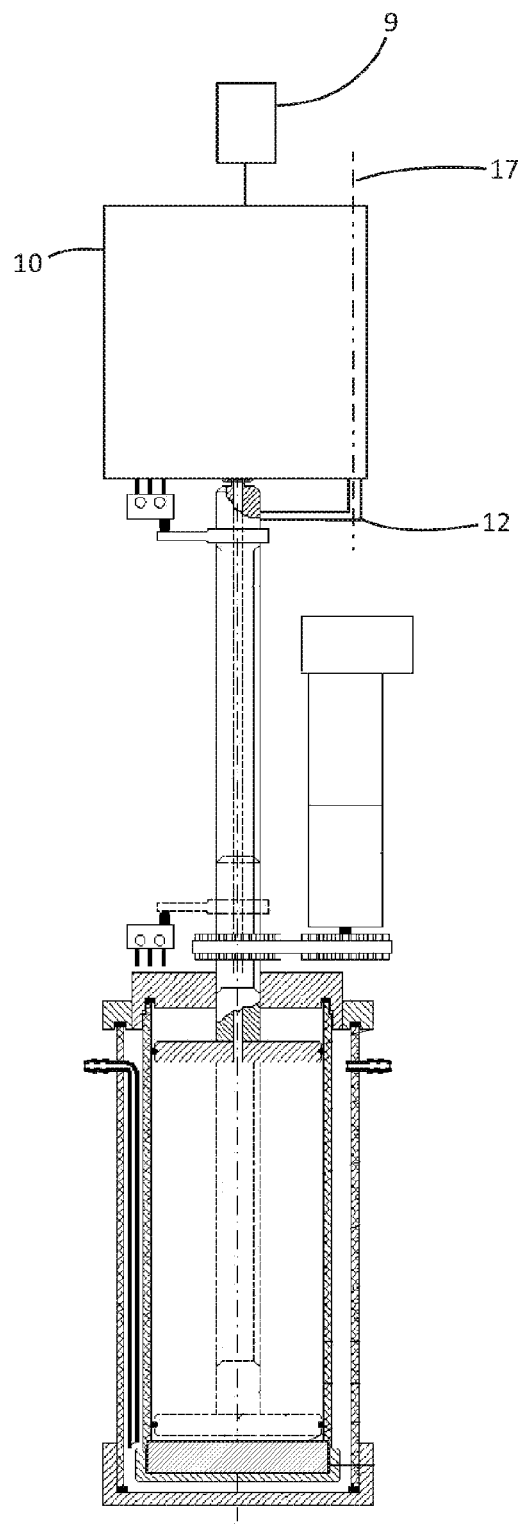
Figures 3, 4, 5, 6:
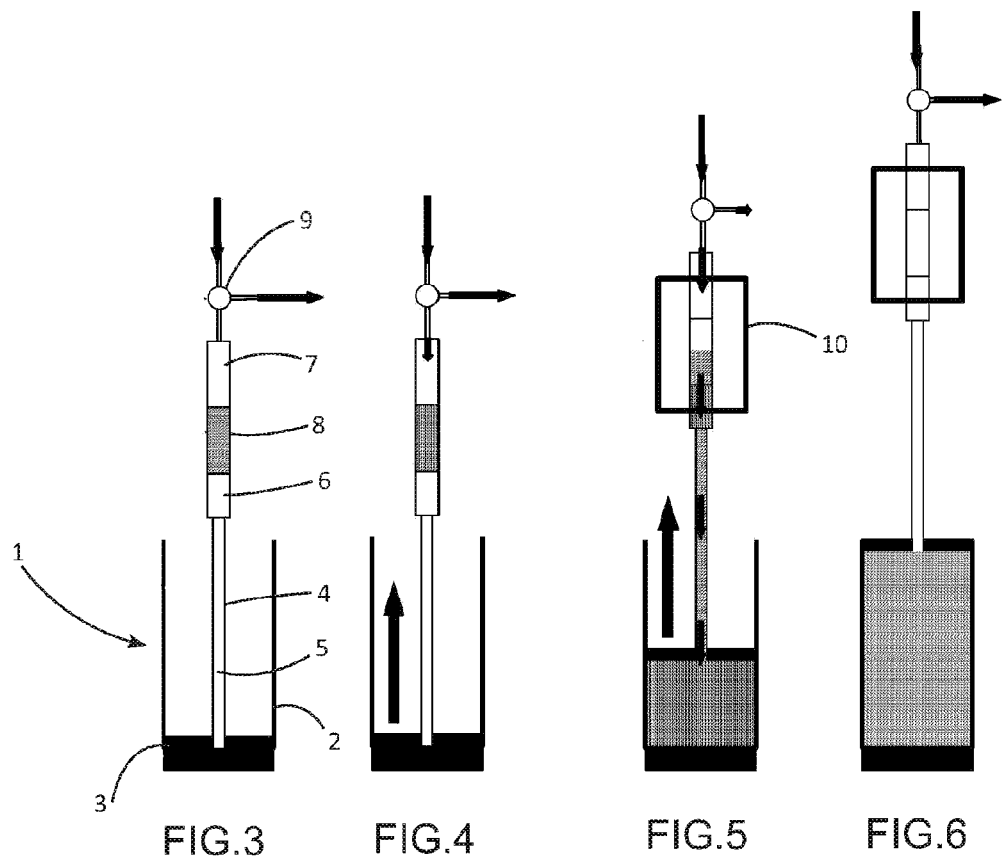

A detailed embodiment of the desorbing method applied to the embodiment of the desorption device of FIGS. 1 and 2 is described hereinafter with reference to FIGS. 3 to 6 and 8.

In a first step 100, the trap 8 containing volatile compounds is secured to the device, especially to the rod 4 of the piston 3 of the device via the securing means 6.

In a second step 110, the flow splitter 9 is secured to the trap via the securing means 7 and the flow splitter is supplied with the carrier gas. To avoid adsorptions of volatile compounds on the surface of the chamber, a moist carrier gas could be used. After this step, the state of the desorption device is illustrated on FIG. 3. The piston is in its lower position and the volume of the chamber is null. The whole flow of the carrier gas supplied to the flow splitter is released in the atmosphere. No carrier gas flows in the trap.

In a third step 120, the motor 20 controlled by the logic processing unit 22 is activated and the piston is moved upward at a controlled speed. Thus, the volume of the chamber increases and a part of the carrier gas supplied to the flow splitter flows through the trap before reaching the chamber. As previously explained, this third step allows to purge oxygen and water from the trap before it is heated. As previously, explained, some moisture in the carrier gas may be advantageous. The speed of the piston obviously defines the flow rate of the carrier gas in the trap. The flow rate of the carrier gas supplied to the flow splitter must be higher than the flow rate of the carrier gas through the trap. If not, other gases than the carrier gas may reach the chamber. However, the flow rate of the carrier gas supplied to the flow splitter must not be very higher than the flow rate of the carrier gas through the trap. If it is, volatile compounds may be released to the atmosphere through the flow splitter. For example, the flow rate ratio is between 1 and 1.5. Preferably, the flow rate ratio is about 1.2. At this step, the state of the desorption device is illustrated on FIG. 4. The trap is at ambient temperature.

In a fourth step 130, the trap is heated. The heating means is switched from its first configuration to its second configuration. The temperature of the trap increases from the ambient temperature to a determined desorbing temperature, for example a temperature comprised between 100° C. and 300° C., especially a temperature of about 250° C.

In a fifth step 140, the motor 20 controlled by the logic processing unit 22 is activated and the piston is moved upward at a controlled speed. Thus, the volume of the chamber increases and a part of the carrier gas supplied to the flow splitter flows through the trap before reaching the chamber. The speed of the piston still defines the flow rate of the carrier gas in the trap. The flow rate of the carrier gas supplied to the flow splitter must still be higher than the flow rate of the carrier gas through the trap. For example, the flow rate ratio is between 1 and 1.5. Preferably, the flow rate ratio is about 1.2. At this step, the state of the desorption device is illustrated on FIG. 5. Desorbed volatile compounds are conveyed from the trap to the chamber in the carrier gas flow. The fourth and fifth steps may be implemented simultaneously. The movement of the piston is stopped when the volume of the chamber reaches a predetermined value or when the piston reaches its upper position. At the end of this step, the state of the desorption device is illustrated on FIG. 6.

In a sixth step 150, the trap is removed from the desorption device. The flow splitter may also be removed from the desorption device.

Figure 9:
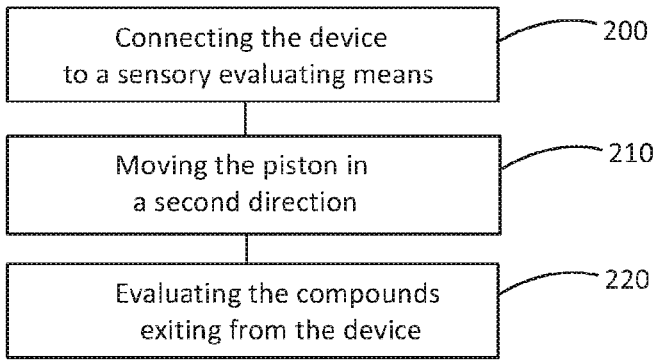

A detailed embodiment of the evaluation method applied to the embodiment of the desorption device of FIGS. 1 and 2 is described hereinafter with reference to FIGS. 7 and 9.

The detailed embodiment of the sensory evaluation method preferably includes the steps 100 to 150. Moreover, it may include the following steps.

In a step 200, the desorption device is connected to a sensory evaluation means.

Then, in a step 210, the motor 20 controlled by the logic processing unit 22 is activated and the piston is moved downward at a controlled speed. Thus, the volume of the chamber decreases and the compounds contained in the chamber are transferred to the sensory evaluation means. Once again, the speed of the piston defines the flow rate of the compounds exiting from the chamber. The downward speed of the piston during the step of transferring compounds to the sensory evaluation means may be different from the upward speed of the piston during the step of desorbing. The downward speed is defined according to the type of the sensory evaluation means so that compounds may be provided to this sensory evaluation means with a defined intensity and/or during a defined time period. At this step, the state of the sensory evaluation device is illustrated on FIG. 7. During this step 210, the chamber temperature may be controlled (e.g. maintained at 50-70° C.), if an adsorption of some volatile compounds on the chamber walls is expected.

The main parameters which may have an impact on the desorption are:

Desorption temperature, set by the temperature of the heating means,
Time period of the purge to evacuate oxygen and water from the trap, before heating it,
Flow rate ratio: flow rate of the carrier gas supplied to the splitter and flow rate of the carrier gas through the trap,
Flow rate of the carrier gas through the trap.

Additional parameters allow to avoid adsorptions of volatile compounds on chamber walls:

Temperature of the piston of the cell chamber,
Moisture of the carrier gas.

EXAMPLE

Pear aroma compounds have been successfully desorbed from a Tenax® trap with the following parameters:
Desorption temperature: 240° C.,
Purge duration: 1.25 min,
Flow rate ratio: 1.2.
Carrier gas flow rate: 20 mL·min$^{-1}$ The devices and/or the methods according to the invention may be used as an odor generator at a constant intensity in e.g. an olfactometer.

The invention allows to faithfully restore the compounds that have been previously trapped. Thus, it allows to faithfully restore the trapped odor.

Moreover, the desorbed compounds may be kept in the chamber. Thus, it is possible to evaluate the odor under controlled parameters. Particularly, it is possible to control the flow rate of the compounds leaving the chamber towards the sensory evaluation means and it is possible to stop then resume a sensory evaluation step.

What is claimed is:

1. A method for restoring a volatile compound that is trapped in a trapping means (8), wherein the method includes the steps of: flowing a carrier gas through the trapping means, at a controlled rate, to a chamber (30) of adjustable volume located downstream of the trapping means by increasing the volume of the chamber; and heating the trapping means during the flowing of the carrier gas therethrough to restore the volatile compound; wherein the heating is provided by moving heating means (10) from a first position remote from the trapping means to a second position close to the trapping means, with the heating means including an inertial element (13) therein that includes a first cut out portion (14) that surrounds at least a portion of the trapping means in the second position, and a thermal insulating material except at the cut out portion; and directing heat to the trapping means by radiation and conduction from the inertia material of the heating means.

2. The method of claim 1, wherein the increase of the volume of the chamber includes a controlled deformation or controlled movement of a wall of the chamber.

3. The method of claim 1, wherein the chamber comprises a cylinder (2) and a piston (3) and wherein the increase of the volume of the chamber includes a controlled movement of the piston in the cylinder.

4. The method of claim 1, wherein the flowing step includes a first flowing sub-step during which the trapping means is not heated.

5. The method of claim 4, wherein the flowing step includes a second flowing sub-step during which the trapping means is heated.

6. The method of claim 1, wherein the carrier gas is a moist carrier gas.

7. The method of claim 1, wherein the chamber is maintained at a predetermined temperature during the increasing of the volume of the chamber.

8. A device (1) for restoring a volatile compound that is trapped in a trapping means (8), wherein the device includes the heating means (10) and hardware means (2, 3, 4, 5, 6, 7, 9, 10, 20, 21, 22) software means for implementing the method according to claim 1.

9. The device according to claim 8, wherein the hardware means includes a chamber (30) and controlling means (20, 21, 22) for controlling the volume of the chamber.

10. The device according claim 8, wherein the controlling means comprises an actuator (20, 21) controlled by a logic processing unit (22), alone or included in a computer, with the actuator controlling deformation or movement of a wall of the chamber.

11. The device according to claim 10, wherein the actuator includes a motor (20).

12. The device according to claim 9, wherein the chamber includes a cylinder (2) and a piston (3).

13. The device according to claim 12, wherein at least one surface of the cylinder or the piston is made of stainless steel that is passivated.

14. The device according to claim 8, wherein the heating means is rotatably mounted on a means (6) for securing the trapping means or on an element (4) directly or indirectly secured to the means (6) for securing the trapping means.

15. The device of claim 12 wherein the trapping means is directly connected to the piston to limit travel distance of the restored compound from the trapping means to the chamber.

16. The method of claim 3 which further comprises directly connecting the trapping means to the piston to limit travel distance of the restored compound from the trapping means to the chamber.

17. The device of claim 15 wherein the trapping means includes securing means (6, 7) on each end and the inertial element (13) includes second (15) and third (16) cut out portions that are larger than the first cut out portion for respectively surrounding the securing means (6, 7), with each cut out portion being U-shaped.

18. The method of claim 16 which further comprises providing securing means (6, 7) on each end of the trapping means and providing second (15) and third (16) cut out portions on the inertial element (13), wherein the second and third cut out portions are larger than the first cut out portion and respectively surround the securing means (6, 7), with each cut out portion being U-shaped.

19. The device of claim 10 wherein the inertial element (13) comprises an electric resistor heater (19) and a temperature sensor (31) for controlling the resistor heater with each of the resistor heater and sensor operatively associated with the logic processing unit (22).

20. The method of claim 1 wherein the inertial element (13) comprises an electric resistor heater (19) and a temperature sensor (31) for controlling the resistor heater with each of the resistor heater and sensor operatively associated with a logic processing unit (22).

* * * * *

UNITED STATES PATENT AND TRADEMARK OFFICE
CERTIFICATE OF CORRECTION

PATENT NO. : 9,222,855 B2  
APPLICATION NO. : 13/820741  
DATED : December 29, 2015  
INVENTOR(S) : Chaintreau et al.

Page 1 of 1

It is certified that error appears in the above-identified patent and that said Letters Patent is hereby corrected as shown below:

In the Claims

Column 10:
Line 12 (claim 8, line 4), after "10, 20, 21, 22)", insert -- or --.

Signed and Sealed this
Twenty-ninth Day of March, 2016

Michelle K. Lee
*Director of the United States Patent and Trademark Office*